(12) United States Patent
Wegner et al.

(10) Patent No.: US 9,810,630 B1
(45) Date of Patent: Nov. 7, 2017

(54) FLUORESCENT MARKING GEL COMPOSITIONS AND METHODS OF USE

(71) Applicant: Ecolab USA Inc., St. Paul, MN (US)

(72) Inventors: Joseph R. Wegner, Falcon Heights, MN (US); Erin Brown, Hager City, WI (US); Xin Sun, Eagan, MN (US); Thomas Mohs, Eagan, MN (US)

(73) Assignee: Ecolab USA Inc., St. Paul, MN (US)

( * ) Notice: Subject to any disclaimer, the term of this patent is extended or adjusted under 35 U.S.C. 154(b) by 405 days.

(21) Appl. No.: 14/204,779

(22) Filed: Mar. 11, 2014

Related U.S. Application Data

(60) Provisional application No. 61/778,134, filed on Mar. 12, 2013.

(51) Int. Cl.
*G01N 21/64* (2006.01)

(52) U.S. Cl.
CPC ......... *G01N 21/64* (2013.01); *G01N 21/6447* (2013.01); *G01N 2021/6439* (2013.01); *G01N 2021/6495* (2013.01); *G01N 2021/6497* (2013.01)

(58) Field of Classification Search
CPC ............... G01N 21/64; G01N 21/6447; G01N 2021/6495; G01N 2021/6497
USPC .......................................... 250/461.1, 484.4
See application file for complete search history.

(56) References Cited

U.S. PATENT DOCUMENTS

| | | | |
|---|---|---|---|
| 5,102,546 A | 4/1992 | Salomon | |
| 5,498,280 A | 3/1996 | Fistner et al. | |
| 5,554,480 A | 9/1996 | Patel et al. | |
| 6,476,385 B1 | 11/2002 | Albert | |
| 7,718,395 B2 | 5/2010 | Carling | |
| 7,780,453 B2 | 8/2010 | Carling | |
| 7,785,109 B2 | 8/2010 | Carling | |
| 8,084,410 B2 | 12/2011 | Carling | |
| 8,236,199 B2 | 8/2012 | Mahany et al. | |
| 8,639,527 B2 | 1/2014 | Rensvold et al. | |
| 2004/0192576 A1 | 9/2004 | Schmid et al. | |
| 2012/0085931 A1 | 4/2012 | Burns et al. | |

FOREIGN PATENT DOCUMENTS

WO    WO2013/112207 AI    8/2013

OTHER PUBLICATIONS

Wacker Chemical Corporation, Cavasol® W7 HP, product data, Version 3.00, Apr. 10, 2005, (2 pages).
Le Fur, Morgane and Soares, Graça M.B., *Improving Optical Brightness of Cellulosic Textiles with β-Cyclodextrins*, from www.fibre2fashion1.com, originally presented at the 88th Textile Institute World Conference Shah Alam, Selangor, Malaysia, May 2012, (8 pages).
Marcolino et al., *Interaction of Curcumin and Bixin with β-Cyclodextrin: Complexation Methods, Stability, and Applications in Food*, J. Agric. Food Chem., 2011, 59(7), pp. 3348-3357.

(Continued)

*Primary Examiner* — David Porta
*Assistant Examiner* — Carolyn Igyarto
(74) *Attorney, Agent, or Firm* — Merchant & Gould P.C.

(57) ABSTRACT

Fluorescing compositions are disclosed for monitoring cleaning of a surface. The fluorescing compositions are stable, fluoresce under UV light, and do not leave a mark after drying and removal. The compositions include an optical brightener solubilized with cyclodextrin.

18 Claims, 1 Drawing Sheet

(56) References Cited

OTHER PUBLICATIONS

Glo Germ™ Company, *Welcome to "Glo Germ™,"* from Jan. 25, 1999 archive at http://web.archive.org/, as printed on Jun. 3, 2014, 3 pages.
Malik et al., *Use of audit tools to evaluate the efficacy of cleaning systems in hospitals*, American Journal of Infection Control (AJIC), vol. 31, No. 3, May 2003, pp. 181-187.
Griffith et al., *An evaluation of hospital cleaning regimes and standards*, Journal of Hospital Infection (2000), vol. 45, revised manuscript accepted Dec. 23, 1999, pp. 19-28.

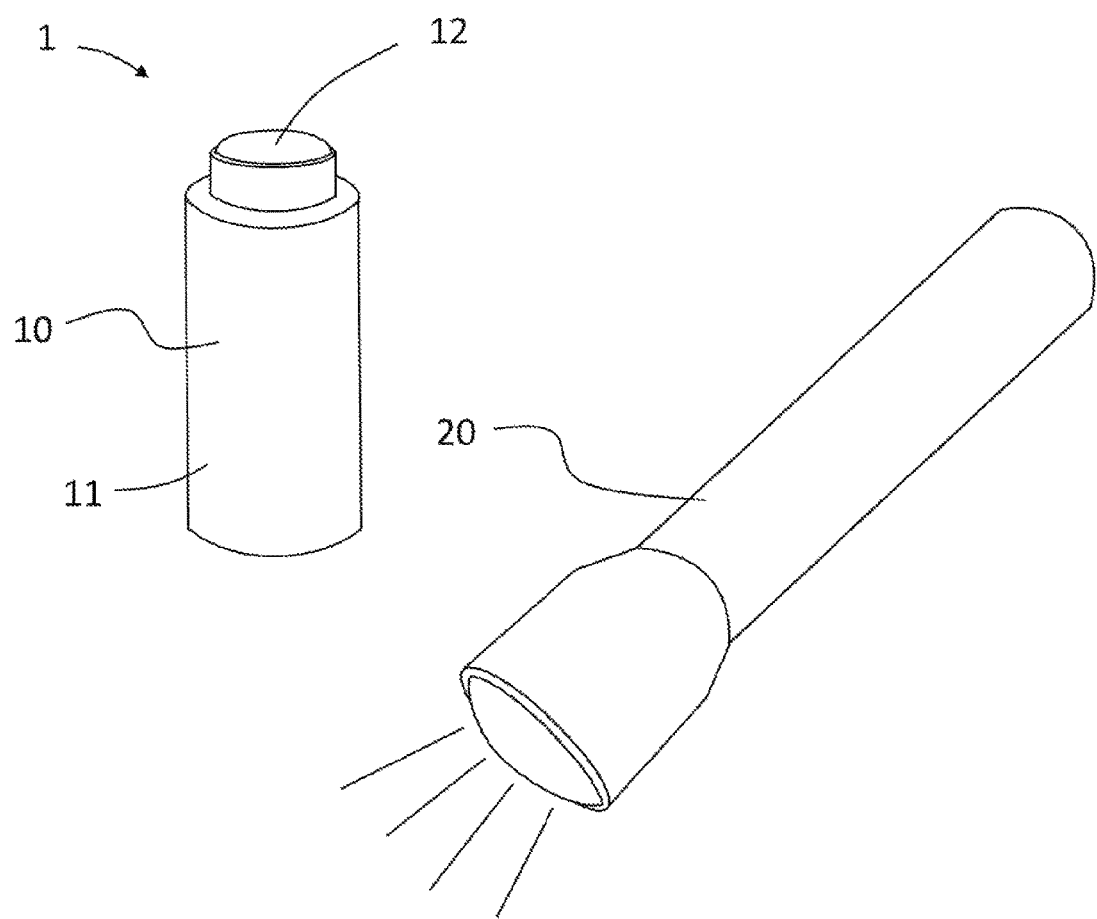

FLUORESCENT MARKING GEL COMPOSITIONS AND METHODS OF USE

CROSS REFERENCE TO RELATED APPLICATIONS

This application claims benefit to U.S. Provisional Application Ser. No. 61/778,134 filed Mar. 12, 2013, which is incorporated herein by reference in its entirety.

BACKGROUND

Currently, more than 1.5 million people develop resistant hospital acquired, i.e., nosocomial, infections in the U.S. annually. Three pathogens posing significant nosocomial problems are MRSA (Methicillin Resistant *Staphylococcus aureus*), VRE (Vancomycin Resistant *Enterococcus*), and *Clostridium difficile* (*C. difficile*). Their importance derives from a combination of resistance to presently available treatments and an ability to rapidly spread extensively in the environment around hospitalized patients. MRSA is present in wound infections, as associated with bed sores and catheters. VRE is present in bowel and urinary tract infections. *C. difficile* is also present in bowel infections and presents as severe diarrhea. For each of these pathogens, control with present antibiotics is problematic, if not impossible.

Enhancement of existing cleaning and disinfection practices deserves further consideration and evaluation. Although it is not currently feasible to define the independent role of the hospital environment in the transmission of health care associated pathogens except in isolated investigations, numerous studies over the past twenty years have confirmed the frequent contamination of many surfaces in the near patient environment with hospital associated pathogens able to survive on inanimate surfaces for weeks to months.

These and similar observations confirm the longstanding belief that environmental cleaning/disinfecting activities are important in providing an optimally safe environment for patients and have led to the development of specific guidelines for environmental infection control in health care facilities.

In view of the above, there is a need for a non-microbiological methodology to evaluate the thoroughness with which housekeeping activities are carried out in hospitals, food service applications, and other industrial, institutional and commercial cleaning of surfaces.

SUMMARY

The disclosed compositions contain a fluorescing optical brightener that can be applied to a surface as a cleaning audit indicator and fully removed through proper cleaning technique In accordance with one aspect of the disclosure, a method for monitoring cleaning of a surface includes applying an amount of the disclosed compositions to an area of a surface and measuring the amount remaining on the surface after cleaning. The disclosed compositions may be fixed to the area of the surface, as by drying. Determining the amount of remaining composition on the surface may include exposing the area to ultraviolet radiation and observing or measuring fluorescence from any remaining composition or by visually observing any remaining composition.

Another aspect of the disclosure relates to compositions for monitoring the cleaning of a surface. The compositions include a carrier, an optical brightener which preferably fluoresces under UV light, and a solublizer which serves to solubilize the optical brightener and assists with the removal of the optical brightener from a surface. The composition may also include a surfactant, a solvent, preservatives and a film-forming agent. The carrier may be water and may also be a detergent. In some embodiments, the disclosed compositions may be fluorescent under ultraviolet radiation. In some embodiment, the composition components are all appropriate for food surfaces and food contact surfaces.

In another aspect, the disclosure relates to a method for monitoring the cleaning of a surface or one or more surfaces where the method includes applying a composition with an optical brightener and a solubilizer, preferably cyclodextrin, to a surface and determining if any of the optical brightener remains on the surface after one or more opportunities to clean the location.

In another aspect, the disclosure relates to a kit for determining if a surface has been cleaned. The kit includes a composition with an optical brightener and a cyclodextrin, an applicator and a blacklight.

These and other embodiments will be apparent to those skilled in the art and others in view of the following description of some embodiments. It should be understood that this summary and the detailed description illustrate only some examples of various embodiments and are not intended to be limiting to the claimed invention.

BRIEF DESCRIPTION OF THE DRAWINGS

FIG. 1 shows an applicator and a blacklight, in accordance with one embodiment.

DETAILED DESCRIPTION

Cleaning of patient rooms is an ongoing process in a hospital. Each patient occupying a room may be subject to pathogens left by a prior occupant of the room and, in turn, may insert his or her specific pathogens into the room environment. An aim of room cleaning is to decrease the likelihood of the environmental transmission of infection to an occupant of the room. Some room sites are cleaned daily while others are cleaned following patient occupation. Generally, such cleaning is unsupervised. Correlation of the health of room occupants could provide an indication of the quality of the cleaning, although with significant effort and with significant delay.

Embodiments of the disclosure as discussed below illustrate where monitoring may provide timely assessment as to whether current cleaning activities are consistent with control over nosocomial infections and may have the potential for objectively evaluating cleaning and disinfecting activities in various health care settings. A nontoxic composition containing an optical brightener which fluoresces with exposure to a black light is inconspicuous yet may be readily removed by housekeeping products. Small volumes of the disclosed composition may be confidentially applied to certain target sites or locations in patient rooms following cleaning and the targets reevaluated following cleaning.

The monitoring method may indicate acceptable cleaning of traditional sites but poor cleaning of other sites which have significant potential for harboring and transmitting microbial pathogens. An integrated program may identify such deficiencies in hospital cleaning and target remediation efforts so as to accelerate reduction in pathogen levels.

For example a hospital room typically comprises a bed in association with bed rails, bed tray, drape, and drape support.

Patient call box and telephone are generally located near the bed and provide communication, where the telephone rests on a table. A chair often is present and provides additional seating. A sink including a faucet, handles, and bedpan flushing device, can provide a cleansing facility. A toilet containing a seat and handle resides in the patient bathroom. A grab bar provides support for a patient in using the toilet. Entry into the room and bathroom is through doors typically via engagement of a handle or push plate. Room lights may be adjusted by a room light switch mounted on a room light switch plate. Bathroom lights may be adjusted by a bathroom light switch mounted on a bathroom light switch plate.

Target locations for monitoring are those which correspond to areas of a surface and may be chosen based on their classification as "high touch" objects (HTOs). Such targets may include a toilet handle, a horizontal surface of toilet bowl, a bedpan flushing device, a horizontal surface of the sink adjacent to the faucet, a doorknob or door handle, or push/grab plate, a toilet area hand hold immediately adjacent to the toilet, a bedside table, a telephone receiver, a call button, an overbed table, a seat target of patient chair, a bedrail adjacent to the head of the bed, a drape, a room light switch, and a bathroom light switch.

To the degree possible, suitable locations for the disclosed compositions include an area which is easily accessible for cleaning and in close proximity to the portion of the object most frequently contaminated by patients' and health care workers' hands. As a consequence of this separation, the composition is not subject to removal by the actions of the patient during the interval between placement of the composition and the subsequent examination of the location. In addition, proximity of the location to areas subject to patient contact makes probable that cleaning of the composition correlates with cleaning of the patient contact areas. An example includes a toilet handle location that is separated from, but in the proximity of the area most likely to receive patient contact during use and be contaminated.

The composition may optionally include and is controllably applied to a location by an applicator or applicator system. The disclosed compositions allow for a broad range of applications including a spray with a spray angle of 5° to 60° or 15° to 30°, a foam pad applicator 10, a shoe-polish-type applicator, felt tip applicator (similar to a highlighter), brush, roll, wipe, a solid form such as an eraser style, solid pen, chalk, etc. The applicator may be a plastic squeeze bottle or a combination of a squeeze bottle or ampule 11 with a foam pad 12 attached to the end. The disclosed compositions may have a viscosity that allows for other methods of application which were not previously acceptable for currently available formulations, such as dispensing into an individual gel applicator or an applicator pad or felt tipped pad as those found on highlighter markers. The compositions may be inconspicuous, transparent, semi-transparent, opaque, or semi-opaque, either in the package, on a surface or both. The compositions may also be environmentally stable, nontoxic, dry rapidly, be readily wetted by spray disinfectants, liquid disinfectants, or other cleaning agents, and be easily removed with light abrasion.

In another aspect, the disclosure relates to a kit 1 for determining if a surface has been cleaned. The kit 1 includes a composition with an optical brightener and a cyclodextrin, an applicator 10 and a blacklight 20.

Compositions

The disclosed compositions include an optical brightener that is solubilized by a cyclodextrin. The disclosed compositions present an improvement over previous fluorescent formulations, which have been found to leave various marks on surfaces. For example, when applied to metal surfaces, previous formulations appeared to leave a mark when they had been applied. This was especially true for surfaces that had been routinely cleaned with a quaternary ammonium compound-based antimicrobial product. When applied to heavily oxidized surfaces or surfaces that have been exposed to UV light, previous compositions appeared to leave a "ghost" mark or faint outline.

While not wanting to be bound by theory, solubilizing the optical brightener in the cyclodextrin appears to improve the removal of the composition from a surface so that it does not leave a mark on surfaces treated with quaternary ammonium compounds or oxidizing chemistry. This is beneficial since quaternary ammonium compounds and oxidizing chemistry are regularly used to disinfect surfaces. It also seems to increase the brightness of the spot on the surface under a blacklight.

The disclosed compositions may be a water-thin liquid, a solid, a thickened liquid, or a gel. If included as a thickened liquid or a gel, the compositions may have a viscosity that allows them to be flowable under pressure (e.g., non-Newtonian fluids). Exemplary viscosities include from about 1500 to about 6000 cps, or from about 2000 to about 4000 cps when measured with a Brookfield viscometer at 25° C. with a #2 spindle at 2.0 rpm.

The disclosed compositions may optionally include other materials, such as a carrier, solvents, surfactants, film-forming polymers, and preservatives.

In some embodiments, the disclosed compositions can be concentrated and then diluted to the disclosed concentration ranges before being used. In some embodiments, the disclosed compositions can be stored in bulk and then divided into dispensers or packages for use. In some embodiments, the disclosed compositions are provided in the desired dispenser at the desired use concentration.

Optical Brightener

The disclosed compositions include an optical brightener to impart fluorescent properties to the composition when viewed with a black light. Exemplary optical brighteners include nonionic, anionic and cationic optical brighteners including triazine-stilbenes, coumarins, imidazolines, diazoles, triazoles, benzoxazolines, biphenyl-stilbenes, benzothioazoles, naphthotriazolylstilbenes, benzimidazoyl, naphthylimide, dianiline, dimorphonline, tetraaniline stilbene triazine stilbenes, derivatives of pyrazolin, cumarin, benzoxazol, naphthalimide, and pyrene, and derivatives and mixtures thereof.

Exemplary commercially available stilbene optical brighteners include Keyfluor AMS-6S, commercially available from Keystone Aniline Corporation and Leocophor FTS, commercially available from Clariant.

Exemplary coumarin optical brighteners include 7-(diethylamino)-4-methyl-2H-1-benzopyran-2-one. Exemplary commercially available coumarin optical brighteners include Keyfluor White RWP, commercially available from Keystone Aniline Corporation, Tinopal SWN (IPA), commercially available from BASF, and Fluorescent Brightener 52.

Exemplary benzoxazoline optical brighteners include 2,2 (2,5-thiophenediyl)bis-5(1,1-dimethylethyl)benzoxazole, 2,2-(1,2-ethenediyldi-4,1-phenylene)bisbenzoxazole, diphenylethylene bisbenzoxazole, 4-methyl-2,2'-(1,2-ethylenediyldi-4,1-phenylene)bisbenzoxazole, 2,5-thiophenedlylbis(5-tert-butyl-1,3-benzoxazole), 1,4-bis(2-benzoxazoly)naphthalene, 1,2-bis(2-benzoxazoly)naphthalene, 2,2-(1,2-ethenediyl-di-4,1-phenylene)bis-5-methyl-benzoxazole, and derivative thereof. Exemplary commercially available benzoxazoline optical brighteners include Hostalux KCBr, commercially available from Clariant and Keyfluor White OB, commercially available from Keystone Aniline Corporation.

Exemplary biphenyl-stilbene optical brighteners include 4,4-bis(5-methyl-2-benzoxazolyl) stilbene, 4,4-bis(2-benzoxazolyl) stilbene, 4,4'-bis[2-(2-methoxyphenyl)ethenyl]-1,1'-diphenyl, benzene-4,4'-bis[2-cyanophenyl)ethenyl], 1,4-bis(cyanostyryl)benzene, benzene-4,4'-bis[2-cyanophenyl) ethenyl], 4,4'-bis(2,2'-cyano-phenylene)-benzene, and derivatives thereof.

Other exemplary optical brighteners include Fluorescent Brightener 101 (CAS #51848-34-1), Fluorescent Brightener 113 (CAS #12768-92-2 (12676-25-4)), Fluorescent Brightener 119 (CAS #12270-52-9), Fluorescent Brightener 121 (CAS #2744-49-2 (12224-11-2)), Fluorescent Brightener 134 (CAS #3426-43-5), Fluorescent Brightener 135 (CAS #1041-00-5 (12224-12-3)), Fluorescent Brightener 184 (CAS #7128-64-5 (12224-40-7)), Fluorescent Brightener 185 (CAS #2866-43-5 (12224-41-8)), Fluorescent Brightener 191 (CAS #12270-53-0), Fluorescent Brightener 204 (CAS #76482-77-4), Fluorescent Brightener 210 (CAS #28950-61-0), Fluorescent Brightener 220 (CAS #16470-24-9), Fluorescent Brightener 251 (CAS #16324-27-9), Fluorescent Brightener 263 (CAS #99549-42-5), Fluorescent Brightener 264 (CAS #76482-78-5), Fluorescent Brightener 264 (CAS #68971-49-3), Fluorescent Brightener 28 (CAS #4193-55-9 (95508-20-6)), Fluorescent Brightener 30 sodium salt (CAS #2606-93-1), Fluorescent Brightener 33 (CAS #61902-19-0), Fluorescent Brightener 351 (CAS #38775-22-3 (54351-85-8)), Fluorescent Brightener 353 (CAS #55585-28-9), Fluorescent Brightener 357 (CAS #41098-56-0 (83512-97-4)), Fluorescent Brightener 363 (CAS #95078-19-6), Fluorescent Brightener 367 (CAS #5089-22-5 (63310-10-1)), Fluorescent Brightener 368 (CAS #117313-08-3), Fluorescent Brightener 378 (CAS #40470-68-6 (164908-53-6)), Fluorescent Brightener 52 (CAS #91-44-1 (61968-71-6; 12224-03-2)), Fluorescent Brightener 54 (CAS #40691-09-6 (12768-89-7)), Fluorescent Brightener 61 (CAS #8066-05-5 (12224-04-3)), Fluorescent Brightener 71 (CAS #16090-02-1), Fluorescent Brightener 85 (CAS #17958-73-5), Fluorescent Brightener 85 (CAS #12224-06-5), Fluorescent Brightener 86 (CAS #12224-07-6), Fluorescent Brightener 87 (CAS #12768-91-1), Fluorescent Brightener 9 (CAS #133-66-4), Fluorescent Brightener 90-1 (CAS #120797-63-9), Fluorescent Brightener CBS-X (CAS #27344-41-8), Fluorescent Brightener ER-III (CAS #79026-03-2), Fluorescent Brightener KS-N (CAS #5242-49-9), Fluorescent Brightening Agent 24 (CAS #12224-02-1), and Fluorescent Brightening Agent 30 (CAS #25738-35-6).

The optical brightener may be present in the composition from about 0.01 to about 10 wt. %, from about 0.01 to about 5 wt. %, and from about 0.01 to about 0.5 wt. %.

Solubilizer

The disclosed compositions include a cyclodextrin solubilizer to solubilize the optical brightener. While not wanting to be bound by theory, it is believed that the cyclodextrin helps solubilize the optical brightener by either coordinating with it or encapsulating it, which not only helps solubilize the optical brightener but also assists with the removal of the optical brightener from a surface.

Cyclodextrins are cyclic molecules of 5, 6, 7, 8, 9, or more sugar molecules. Cyclodextrins are found in three configurations—alpha, beta, and gamma—with chemical substitutions of the 2-, 3-, and 6-hydroxyl sites. Exemplary substitutions include but are not limited to hydroxypropyl-, methyl-, and hydroxyethyl-groups. Exemplary cyclodextrins for use in the disclosed compositions include but are not limited to α-cyclodextrin, β-cyclodextrin, γ-cyclodextrin, (2-hydroxypropyl)-β-cyclodextrin, (2-hydroxypropyl)-γ-cyclodextrin, methyl-β-cyclodextrin, and mixtures thereof. A preferred cyclodextrin is methyl-β-cyclodextrin.

The solubilizer may be present in the composition from about 0.1 to about 50 wt. %, from about 0.5 to about 25 wt. %, and from about 1 to about 10 wt. %.

Film Forming Agent

The disclosed compositions may optionally include a film forming agent. The film forming agent provides a means to reduce inadvertent smearing of the product before cleaning and as a means of modifying the viscosity of the product for application. Exemplary film forming agents include, but are not limited to, xanthan gum, hydroxypropyl cellulose, hydroxyethyl cellulose, hydroxypropyl methyl cellulose, hydrophobically modified hydroxyl ethylcellulose, hydrophobically modified hydroxypropyl cellulose, guar gum, polyacrylate copolymers, vinylacetate/alcohol copolymers, casein, urethane copolymers, dimethicone PEG-8 polyacrylate, modified starch, poly(DL-lactic-co-glycolic acid), polypeptide polymers and oligomers, and other polysaccharide polymers and oligomers, high molecular weight polyethylene glycol and polyethylene glycol polypropylene glycol copolymers.

The film forming agent may be present in the composition from about 0.01 to about 15 wt. %, from about 0.1 to about 5 wt. %, and from about 0.1 to about 1 wt. %.

Surfactant

The disclosed compositions may optionally include a surfactant to assist the composition in depositing on a surface as a layer and not bead up on the surface.

Exemplary anionic surfactants include any anionic surfactant available in the cleaning industry. Suitable groups of anionic surfactants include sulfonates and sulfates. Suitable surfactants include alkyl aryl sulfonates, secondary alkane sulfonates, alkyl methyl ester sulfonates, alpha olefin sulfonates, alkyl ether sulfates, alkyl sulfates, and alcohol sulfates.

Exemplary alkyl aryl sulfonates that can be used can have an alkyl group that contains 6 to 24 carbon atoms and the aryl group can be at least one of benzene, toluene, and xylene. A suitable alkyl aryl sulfonate includes linear alkyl benzene sulfonate. A suitable linear alkyl benzene sulfonate includes linear dodecyl benzyl sulfonate that can be provided as an acid that is neutralized to form the sulfonate. Additional suitable alkyl aryl sulfonates include xylene sulfonate and cumene sulfonate.

Exemplary alkane sulfonates that can be used can have an alkane group having 6 to 24 carbon atoms. Suitable alkane sulfonates that can be used include secondary alkane sulfonates. A suitable secondary alkane sulfonate includes sodium $C_{14}$-$C_{17}$ secondary alkyl sulfonate commercially available as Hostapur SAS from Clariant.

Exemplary alkyl methyl ester sulfonates that can be used include those having an alkyl group containing 6 to 24 carbon atoms. Exemplary alpha olefin sulfonates that can be used include those having alpha olefin groups containing 6 to 24 carbon atoms.

Exemplary alkyl ether sulfates that can be used include those having between about 1 and about 10 repeating alkoxy groups, or between about 1 and about 5 repeating alkoxy groups. In general, the alkoxy group will contain between about 2 and about 4 carbon atoms. A suitable alkoxy group is ethoxy. A suitable alkyl ether sulfate is sodium lauryl ether sulfate and is available under the name Steol CS-460.

Exemplary alkyl sulfates that can be used include those having an alkyl group containing 6 to 24 carbon atoms. Suitable alkyl sulfates include, but are not limited to, sodium lauryl sulfate and sodium lauryl/myristyl sulfate.

Exemplary alcohol sulfates that can be used include those having an alcohol group containing about 6 to about 24 carbon atoms.

The anionic surfactant can be neutralized with an alkaline metal salt, an amine, or a mixture thereof. Suitable alkaline metal salts include sodium, potassium, and magnesium. Suitable amines include monoethanolamine, triethanolamine, and monoisopropanolamine.

If a mixture of salts is used, a suitable mixture of alkaline metal salt can be sodium and magnesium, and the molar ratio of sodium to magnesium can be between about 3:1 and about 1:1.

Nonionic surfactants that can be used include polyalkylene oxide surfactants (also known as polyoxyalkylene surfactants or polyalkylene glycol surfactants). Suitable polyalkylene oxide surfactants include polyoxypropylene surfactants and polyoxyethylene glycol surfactants. Suitable surfactants of this type are synthetic organic polyoxypropylene (PO)-polyoxyethylene (EU) block copolymers. These surfactants include a di-block polymer comprising an EU block and a PO block, a center block of polyoxypropylene units (PO), and having blocks of polyoxyethylene grafted onto the polyoxypropylene unit or a center block of EO with attached PO blocks. Further, this surfactant can have further blocks of either polyoxyethylene or polyoxypropylene in the molecules. A suitable average molecular weight range of useful surfactants can be about 1,000 to about 40,000 and the weight percent content of ethylene oxide can be about 10-80 wt %.

Additional nonionic surfactants include alcohol alkoxylates. A suitable alcohol alkoxylate includes linear alcohol ethoxylates such as Tomadol™ 1-5 which is a surfactant containing an alkyl group having 11 carbon atoms and 5 moles of ethylene oxide. Additional alcohol alkoxylates include alkylphenol ethoxylates, branched alcohol ethoxylates, secondary alcohol ethoxylates (e.g., Tergitol 15-S-7 from Dow Chemical), castor oil ethoxylates, alkylamine ethoxylates, tallow amine ethoxylates, fatty acid ethoxylates, sorbital oleate ethoxylates, end-capped ethoxylates, or mixtures thereof. Additional nonionic surfactants include amides such as fatty alkanolamides, alkyldiethanolamides, coconut diethanolamide, lauric diethanolamide, polyethylene glycol cocoamide (e.g., PEG-6 cocoamide), oleic diethanolamide, or mixtures thereof. Additional suitable nonionic surfactants include polyalkoxylated aliphatic base, polyalkoxylated amide, glycol esters, glycerol esters, amine oxides, phosphate esters, alcohol phosphate, fatty triglycerides, fatty triglyceride esters, alkyl ether phosphate, alkyl esters, alkyl phenol ethoxylate phosphate esters, alkyl polysaccharides, block copolymers, alkyl polyglucosides, or mixtures thereof. An alcohol alkoxylate nonionic surfactant is a preferred surfactant.

Exemplary amphoteric surfactants include, but are not limited to: betaines, imidazolines, propionates, sultaines, amphopropionates, amphodipropionates, aminopropionates, aminodipropionates, amphoacetates, amphodiacetates, and amphohydroxypropylsulfonates.

Exemplary cationic surfactants that can be used include, but are not limited to: amines such as primary, secondary and tertiary monoamines with $C_{18}$ alkyl or alkenyl chains, ethoxylated alkylamines, alkoxylates of ethylenediamine, imidazoles such as a 1-(2-hydroxyethyl)-2-imidazoline, a 2-alkyl-1-(2-hydroxyethyl)-2-imidazoline, and the like; and poly phosphate ammonium salts, as for example, alkylpoly phosphate ammonium chloride surfactants such as n-alkyl ($C_{12}$-$C_{18}$)dimethylbenzyl ammonium chloride, n-tetradecyldimethylbenzylammonium chloride monohydrate, and a naphthylene-substituted poly phosphate ammonium chloride such as dimethyl-1-naphthylmethylammonium chloride.

Exemplary cationic surfactants include dialkylamido ethyl hydroxyethylmonium salt, dialkylamidoethyl dimonium salt, dialkyloyl ethyl hydroxyethylmonium salt, dialkyloyl ethyldimonium salt, and mixtures thereof; for example, commercially available under the following tradenames: VARIS OFT 110, VARISOFT 222, VARIQUAT K1215 and VARIQUAT 638 from Witco Chemicals, MACKPRO KLP, MACKPRO WLW, MACKPRO MLP, MACKPRO NSP, MACKPRO NLW, MACKPRO WWP, MACKPRO NLP, MACKPRO SLP from McIntyre, ETHOQUAD 18/25, ETHOQUAD O/12PG, ETHOQUAD C/25, ETHOQUAD S/25, and ETHODUOQUAD from Akzo, DEHYQUAT SP from Henkel, and ATLAS G265 from ICI Americas.

Additional surfactants include silicone surfactants such as PEG/PPG-20/15 dimethicone silicone polyether copolymer, PEG-12 dimethicone silicone polyether copolymer, PEG-10 dimethicone silicone polyether copolymer, PEG-17 dimethicone silicone polyether copolymer, PPG-12 dimethicone silicone polyether copolymer, PEG/PPG 20/23 dimethicone silicone copolymer, polyether silicones, trisiloxane ethoxylates, amino silicones, silicone betaines, silicone quats, and derivatives and mixtures thereof. Exemplary commercially available silicone surfactants include SF1188A, SF1288, Silsoft 860, Silsoft 880, Silsoft 895, Silsoft 900, Silsoft 440, Silwet L-7607, Silwet L77, Silwet Hydrostable 212, Silwet Hydrostable 611, Silwet 408, Silwet 618, and the Dow Corning® 5-7113 silicone quat.

The surfactant may be present in the composition from about 0 to about 40 wt. %, from about 0.01 to about 20 wt. %, and from about 0.01 to about 10 wt. %.

Solvent

The disclosed compositions may optionally include a solvent to assist with solubility and shorten the drying time of the composition on a surface. Exemplary solvents include, but are not limited to, water, isopropanol, methanol, ethanol, n-propanol, n-butanol, 2-butanol, benzyl alcohol, propylene glycol, ethylene glycol, glycerine, 1,2-propanediol, hexanol, benzyl alcohol, dipropylene glycol, acetic acid, formic acid, propanoic acid, acetone, acetonitrile, 1,2-butane diol, 1,3-butanediol and the like and mixtures thereof.

The solvent may be present in the composition from 0 to about 70 wt. %, from about 0.01 to about 50 wt. %, and from about 0.01 to about 10 wt. %.

Additional Agents

The disclosed compositions may include a variety of ingredients, including but not limited to a preservative and UV stabilizers.

Preservatives

The disclosed compositions may optionally include a preservative to prevent microorganisms from growing in the composition. Exemplary preservatives include, but are not limited to, phenoxyethanol, benzoic acid salts, sorbate salts, parabans such as methyl, propyl, isobutyl and butyl, methylisothiazolinone, methylchloroisothiazolinone, ethylhexylglycerin, caprylylglycol, hexylene glycol, 2-bromo-2-nitropropane-1,3-diol, piroctone olamine, glyceryl caprylate, dimethyl dimethylol hydantoin, diazolidinyl urea, polyaminopropyl biguanide, sodium hydroxymethylglycinate, phenoxyisopropanol, thyme leaf extract, iodopropynyl butylcarbamate, imidazolidinyl urea, benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide.

The preservative may be present in the composition from 0 to about 5 wt. %, from about 0.01 to about 2.5 wt. %, and from about 0.01 to about 1 wt. %.

UV Stabilizers

The disclosed compositions may optionally include materials to help stabilize the optical brightener such as an antioxidant like butylated hydroxyanisole, butylated hydroxytoluene, propyl gattate, vitamin A, vitamin E, vitamin C, polyphenols, and salicylic acid.

Methods of Using the Disclosed Compositions

Before cleaning a room, the composition may be deposited on surfaces such as those indicated herein and fixed to the surface, as, for example, by being allowed to dry. Since the dried composition does not occupy a location likely to encounter abrasion from daily activities, its removal may be assumed to be the result of cleaning activities. When the dried composition is transparent, semi-transparent or inconspicuous, those engaged in cleaning activities are unaware of its location. Consequently, they are not biased to clean areas adjacent to the composition and to avoid the composition or to focus on the location with the composition without cleaning the remainder of the surface.

After a single cleaning opportunity or multiple cleaning opportunities are presented, cleaning activities may be suspended, for example for a day or less, between a day and a week, or between a week and a month. That is, further cleaning in the room may not be permitted until the locations with the compositions within the room are scanned. The locations within a room may then be scanned with a device able to render visible the dried composition so as to reveal the extent to which the location and therefore the composition have been subjected to cleaning. A location may be considered to have been cleaned if the dried composition was removed or clearly disturbed. If the composition contains a material that fluoresces under exposure to ultraviolet radiation, a UV source may be held over the target locations to reveal dried composition not removed during cleaning.

In the disclosed methods, whether the composition has been removed or not from a specific location can be recorded, for example, on a tracking sheet or in a database (e.g., using a computer, tablet, smart phone, iPod or other device) to create individual datapoints for whether a location was adequately cleaned. Data collected from multiple locations can be compiled and evaluated to give a cleaning result that is indicative or representative of how clean a space (e.g., a room, floor, building, hospital, hospital network) is. The more compositions that have been removed, the cleaner an area is. This data can be used to make comparisons such as between two different locations, between a location and a baseline, standard or goal, or between two different time points for the same location. The baseline, standard, or goal data can be data that was collected before any cleaning program or training was implemented. The baseline, standard, or goal data could be the best practice in the industry or within a particular facility or group of facilities (e.g., within a hospital system or network). The baseline, standard, or goal data could also be an average of various facilities. The collected data can also be used for training environmental services or housekeeping staff on cleaning techniques, cleaning locations, or how to improve cleaning and therefore cleaning scores. The data can be reported with a hardcopy report or with a virtual report that is available online, via email, or via an application or database. An example of a data collecting and reporting system is found in U.S. Pat. No. 8,639,527, which is incorporated herein by reference in its entirety.

Exemplary UV light sources include lights with UV in the range of 360-410 nm with a preferred range of excitation wavelength of 365-390 nm. This wavelength range is selective enough so that all surfaces do not appear fluorescent under the light, but that the dried composition is easily identified when viewed under the UV light. The UV light source may be a pen, wand, or flashlight. The source is preferably a pen with a radiation cone angle of 5-40°, 10-30° or 15-20°.

The disclosed compositions have several advantages over other commercially available formulas. In some embodiments, the disclosed compositions form a stable formulation which has a viscosity suitable for application through a foam applicator pad or felt tipped pad as those found on highlighter markers. Other prior formulas have a viscosity which was too high for this type of application and resulted in a thick glob when dabbed onto a surface. This glob dried to a rough sticky solid clearly visible where applied. The current formulation also has a viscosity suitable for dispensing into an individual gel applicator. The compositions are also low foaming and quick drying to the surface and do not leave any rough or sticky residue.

When the disclosed compositions are applied to the surface and allowed to dry, they are easy to remove by standard cleaning and can be removed without scrubbing. And as described above, the disclosed compositions do not leave a mark on the surface and appear brighter under a UV light than compositions without the addition of cyclodextrin.

Methods of Making the Disclosed Compositions

The film-forming polymer and water are preferably blended together first while stirring to allow the solution to thicken. Stirring may take up to 30 minutes to complete the process and for the solution to achieve the desired consistency. The solution may also be heated to approximately 50° C. to aid in the process. Other components are then simply added while stirring. The composition may then be further processed as desired and as known in the art for creating various gel thicknesses or even solids.

The following examples and test data provide an understanding of certain specific embodiments. The examples are not meant to limit the scope that has been set forth in the foregoing description. Variations within the disclosed concepts are apparent to those skilled in the art.

EXAMPLES

Example 1

Example 1 determined the effect of multiple cyclodextrin-based solubilizers on the solubility of the nonionic optical brightener Keyfluor AMS-6x in solution and the removability of the optical brighteners from a surface. This example tested the following formulas.

TABLE 1

| Formulation | Keyfluor | Cavasol W7 M (50%) | Cavasol W7 HP | Cavamax W7 | Cavamax w8 | Isopropanol (99%) | water | Solution clarity: Clear (C), Hazy (H), insoluble (P) |
|---|---|---|---|---|---|---|---|---|
| A | 0.21 | 4.048 | 0 | 0 | 0 | 0 | 95.742 | H |
| B | 0.21 | 0 | 3.033 | 0 | 0 | 0 | 96.757 | H |
| C | 0.175 | 0 | 0 | 2.97 | 0 | 0 | 96.854 | P |
| D | 0.101 | 0 | 0 | 0 | 3.01 | 0 | 96.889 | C |
| E | 0.2 | 8.055 | 0 | 0 | 0 | 0 | 91.745 | H |
| F | 0.209 | 0 | 0 | 0 | 0 | 0 | 99.791 | P |
| G | 0 | 4.004 | 0 | 0 | 0 | 0 | 95.996 | C |
| H | 0.1 | 2.041 | 0 | 0 | 0 | 0 | 97.859 | H |
| I | 0.109 | 2.69 | 0 | 0 | 0 | 0 | 97.201 | H |
| J | 0.15 | 0 | 0 | 3.192 | 0 | 0 | 96.659 | P |
| K | 0.145 | 9.644 | 0 | 0 | 0 | 4.822 | 85.389 | P |
| L | 0.15 | | | | | 99.85 | | P |
| A* | 0.194 | 6.601 | 0 | 0 | 0 | 4.651 | 88.554 | C |
| B* | 0.209 | 0 | 3.274 | 0 | 0 | 0 | 96.517 | C |
| E* | 0.187 | 14.138 | 0 | 0 | 0 | 0 | 85.676 | C |
| H* | 0.1 | 2.539 | 0 | 0 | 0 | 0 | 97.362 | C |

Some of these formulas were then evaluated on different surfaces to determine if they left a mark and were easily removable. The formulas were tested against gray formica, black-coated particleboard, and white-coated particleboard. Before the test, the surfaces had been treated 10 times with one of the following antimicrobial products: Dispatch® Hospital Cleaner Disinfectant Towels with Bleach, which is a halogen bleach-based wipe commercially available from the Clorox Professional Products Company; a 3 oz/gallon dilution of OxyCide, which is a peracetic acid antimicrobial composition commercially available from Ecolab Inc.; or a 2 oz/gallon dilution of Quaternary Disinfectant Cleaner, which is a quaternary ammonium compound antimicrobial composition commercially available from Ecolab Inc. Treating the surface simulated the charge buildup encountered on hospital surfaces that are regularly treated with antimicrobial products. The various antimicrobial products were liberally applied to the surfaces and allowed to dry at ambient temperatures.

To evaluate the optical brightener, a grid was drawn on the surfaces with 15 mm×15 mm squares, and test products were applied using a cotton tipped swab to an area of the grid. The tester was blind to the contents of the different test products. The test product was washed off using a microfiber cloth soaked in water and light manual scrubbing. The degree of removal was scored by visual assessment of the mark using a 365 nm UV light. The degree of removal was graded on the following scale: 1=complete removal; 2=slight visible fluorescence (5-20%); 3=visible fluorescence (20-40%); 4=significant fluorescence (40-60%); and 5=fluorescent (60-100%). Samples that showed no fluorescence were excluded from the results as well as products with incomplete solubility. The results are shown in Table 2.

TABLE 2

| treatment | QDC | | | Bleach | | | OxyCide | | |
|---|---|---|---|---|---|---|---|---|---|
| surface | black | White | formica | black | white | mica | black | white | mica |
| A* | 1 | 1 | 1 | 1 | 1 | 1 | 1 | 1 | 2 |
| B* | 1 | 1 | 1 | 1 | 1 | 1 | 1 | 1 | 2 |
|  | (halo) | (halo) | (halo) | | | | | | |
| D | 2 | 2 | 2 | 1 | 1 | 1 | 1 | 2 | 2 |
| E* | 1 | 1 | 1 | 1 | 1 | 1 | 1 | 1 | 1 |
| F^ | 3 | 3 | 2 | 1 | 1 | 1 | 2 | 2 | 3 |
| G | no initial fluorescence | | | | | | | | |
| H* | 1 | 2 | 1 | 1 | 1 | 1 | 1 | 1 | 1 |

^samples not entirely soluble
*adjusted sample from formulation table

Formulas A*, B*, E* had good results with Formula E* providing the best results with complete removal and no halo across all surfaces and all treatments. Formulas C and I were not tested because they did not provide a homogeneous system in that particles or insoluble material were observed in the formulation.

Example 2

Example 2 determined the effect of the optical brightener selection on the solubility of the optical brightener and the removability of the optical brightener from a surface. For this example, Cavasol W7M was used as the cyclodextrin solubilizer. This example used the formulations in Table 3.

TABLE 3

| Formulation | Cavasol W7M | Leocophor FTS | Hostalux ACK | Hostalux KCBr | Tinopoal CBS-x | Pylaklor S17A | Keyfluor white RWP | Keyfluor white OB | Tinopal SWN (IPA) | Isopropanol | water | Solution clarity: Clear (C), Hazy (H), insoluble (P) |
|---|---|---|---|---|---|---|---|---|---|---|---|---|
| AA | 4.03 | 0.20 | | | | | | | | | 95.77 | C |
| BB | 4.09 | | 0.19 | | | | | | | | 95.72 | C |
| CC | 4.07 | | | 0.18 | | | | | | | 95.75 | P |
| DD | 4.10 | | | | 0.20 | | | | | | 95.70 | C |
| EE | 3.97 | | | | | 0.20 | | | | | 95.83 | C |
| FF | 4.03 | | | | | | 0.20 | | | | 95.77 | C |
| GG | 5.17 | | | | | | | 0.19 | | | 94.64 | P |
| HH | 4.08 | | | | | | | | 0.18 | | 95.74 | C |
| I I | 0.00 | 0.20 | | | | | | | | | 99.80 | C |
| JJ | 0.00 | | 0.20 | | | | | | | | 99.80 | C |
| KK | 0.00 | | | 0.20 | | | | | | | 99.80 | P |
| LL | 0.00 | | | | 0.21 | | | | | | 99.79 | C |
| MM | 0.00 | | | | | 0.23 | | | | | 99.77 | C |
| NN | 0.00 | | | | | | 0.19 | | | | 99.81 | P |
| OO | 0.00 | | | | | | | | | | 99.80 | P |
| PP | 0.00 | | | | | | | | 0.20 | | 99.80 | P |
| QQ | 0.00 | | | | | | | 0.13 | | 99.87 | | C |
| GG* | 15.50 | | | | | | | 0.17 | | | 84.33 | P |

These formulas were tested using the same procedure as in Example 1. The results are shown in Table 4.

TABLE 4

| treatment | QDC | | | Bleach | | | OxyCide | | |
|---|---|---|---|---|---|---|---|---|---|
| surface | black | White | formica | black | white | formica | black | white | formica |
| AA | 1 | 2 | 3 | 2 | 2 | 1 | 1 | 1 | 2 |
| II | 1 | 1 | 1 | 3 | 1 | 2 | 1 | 1 | 2 |
| BB | 1 | 1 | 1 | 1 | 1 | 1 | 1 | 1 | 1 |
| JJ | 1 | 1 | 1 | 1 | 1 | 1 | 1 | 1 | 2 |
| DD | 3 | 3 | 2 (halo) | 1 | 1 | 2 | 1 | 1 | 2 |
| LL | 3 | 4 | 3 | 1 | 1 | 1 | 1 | 2 | 3 |
| EE | 1 | 1 | 1 | 1 | 1 | 1 | 1 | 1 | 1 |
| MM | 1 | 1 | 1 | 1 | 1 | 1 | 1 | 2 | 2 |
| FF | 1 | 1 | 1 | 1 | 1 | 1 | 1 | 1 | 1 |
| NN^ | Not soluble | | | | | | | | |
| QQ | 3 | 2 | 2 | 1 | 1 | 2 | 2 | 1 | 2 |
| GG* | Not soluble | | | | | | | | |
| OO^ | Not soluble | | | | | | | | |
| HH | 1 | 1 | 1 | 1 | 1 | 1 | 1 | 1 | 1 |
| PP^ | Not soluble | | | | | | | | |

^System not fully soluble
*adjusted sample from formulation table

Formulas BB, EE, FF, HH, JJ, and MM had good results with Formulas BB, EE, FF, and HH providing complete removal and no halo across all surfaces and all treatments. Formulas CC, GG, KK, NN, OO and PP were not tested because they did not provide a homogeneous system in that particles or insoluble material were observed in the formulation.

The above specification, examples and data provide a complete description of the manufacture and use of the present disclosure. Since many embodiments can be made without departing from the spirit and scope of the disclosure, the invention resides in the claims.

We claim:

1. A method for determining if a location in a space has been cleaned comprising:
    a) applying a composition to a location on an environmental surface, the composition comprising:
        i) a nonionic optical brightener; and
        ii) a β-cyclodextrin; and
    b) determining if any of the optical brightener remains on the location after the space has been cleaned.

2. The method of claim 1, the composition further comprising a film forming agent.

3. The method of claim 1, the composition further comprising a surfactant.

4. The method of claim 1, the composition further comprising a solvent.

5. The method of claim 1, the composition further comprising a preservative.

6. The method of claim 1, the composition further comprising an antioxidant.

7. The method of claim 1, wherein the location is selected from the group consisting of a toilet handle, a horizontal surface of a toilet bowl, a bedpan flushing device, a horizontal surface of a sink adjacent to a faucet, a doorknob or door handle, a push plate, a grab plate, a toilet area hand hold, a bedside table, a telephone receiver, a call button, an overbed table, a seat target of patient chair, a bedrail, a drape, a room light switch, a bathroom light switch, and combinations thereof.

8. The method of claim 1, wherein determining if any optical brightener remains on the location comprises exposing the location to UV radiation so that any remaining optical brightener will fluoresce.

9. The method of claim 1, wherein determining if any optical brightener remains on the location comprises visually observing the location to see if there is any remaining optical brightener.

10. The method of claim 1, wherein the presence or the removal of the optical brightener provides a cleaning result.

11. The method of claim 1, wherein the composition does not leave a mark on the location after it has been removed.

12. The method of claim 1, wherein the presence or the removal of the optical brightener provides a measureable cleaning result.

13. A method for determining if one or more locations in a space have been cleaned comprising:

a) applying a composition to a location on one or more environmental surfaces, the composition comprising:
   i) a nonionic optical brightener; and
   ii) a β-cyclodextrin; and
b) determining if any of the optical brightener remains on the location after the space has been cleaned;
c) recording results of step b) to generate data; and
d) compiling the data into a report.

14. The method of claim 13, wherein the report is a printed report.

15. The method of claim 13, wherein the report is a virtual report.

16. The method of claim 13, wherein the location is selected from the group consisting of a toilet handle, a horizontal surface of a toilet bowl, a bedpan flushing device, a horizontal surface of a sink adjacent to a faucet, a doorknob or door handle, a push plate, a grab plate, a toilet area hand hold, a bedside table, a telephone receiver, a call button, an overbed table, a seat target of patient chair, a bedrail, a drape, a room light switch, a bathroom light switch, and combinations thereof.

17. The method of claim 13, wherein determining if any optical brightener remains on the location comprises exposing the location to UV radiation so that any remaining optical brightener will fluoresce.

18. A kit for determining whether a surface has been cleaned comprising:
a) a composition comprising:
   i) a nonionic optical brightener; and
   ii) a β-cyclodextrin;
b) an applicator comprising an ampule with a foam applicator pad; and
c) a blacklight.

* * * * *